US007766839B2

(12) United States Patent
Rogers et al.

(10) Patent No.: US 7,766,839 B2
(45) Date of Patent: Aug. 3, 2010

(54) NEEDLE INSERTION SYSTEMS AND METHODS

(75) Inventors: Peter H. Rogers, 750 Park Ave., Apt. 19N, Atlanta, GA (US) 30326; David H. Trivett, 36 28th St., Atlanta, GA (US) 30309; Francois Guillot, 628 Stokeswood Ave., Atlanta, GA (US) 30316; Michael Dean Gray, 3077 Vinings Ridge Dr., Atlanta, GA (US) 30339; James W. Larsen, 477 Oakleaf Trail, Suwanee, GA (US) 30024

(73) Assignees: Peter H. Rogers, Atlanta, GA (US); David H. Trivett, Atlanta, GA (US); Francois Guillot, Atlanta, GA (US); Michael Dean Gray, Atlanta, GA (US); James W. Larsen, Suwanee, GA (US)

( * ) Notice: Subject to any disclaimer, the term of this patent is extended or adjusted under 35 U.S.C. 154(b) by 927 days.

(21) Appl. No.: 10/897,663

(22) Filed: Jul. 22, 2004

(65) Prior Publication Data

US 2005/0033177 A1    Feb. 10, 2005

Related U.S. Application Data (60) Provisional application No. 60/489,125, filed on Jul. 22, 2003.

(51) Int. Cl.
*A61B 8/00* (2006.01)
(52) U.S. Cl. .................. 600/461; 600/407; 600/443; 600/453; 600/454; 600/459; 604/116; 604/179; 606/181; 606/185

(58) Field of Classification Search .................. 600/407, 600/443, 453, 454, 459, 461; 604/116, 179; 606/181, 185
See application file for complete search history.

(56) References Cited

U.S. PATENT DOCUMENTS

| 3,556,079 A | | 1/1971 | Omizo et al. | |
| 4,325,381 A | * | 4/1982 | Glenn | 600/446 |
| 4,527,569 A | | 7/1985 | Kolb | 128/660 |
| 4,667,679 A | | 5/1987 | Sahota | |
| 4,742,829 A | * | 5/1988 | Law et al. | 600/461 |

(Continued)

OTHER PUBLICATIONS

Peter H. Rogers, David H. Trivett, Michael D. Gray, James W. Larsen, Invention Disclosure for A Device for Locating Veins and Aligning and Inserting Intravenous Catheters and Blood Drawing Needles Therein, Jul. 17, 2003, Georgia Institute of Technology, Atlanta, GA 30328.

*Primary Examiner*—Brian Casler
*Assistant Examiner*—John F Ramirez
(74) *Attorney, Agent, or Firm*—Thomas, Kayden, Horstemeyer & Risley, LLP (57) ABSTRACT

Embodiments of a needle insertion system and method are disclosed. One method embodiment includes transmitting a sound beam along an axis to contact a blood vessel; receiving the reflected sound beam from the blood vessel; processing the reflected sound beam to detect the location of the blood vessel; and, responsive to the detection, receiving a needle in a guideway that is oriented parallel to the axis.

22 Claims, 10 Drawing Sheets

U.S. PATENT DOCUMENTS

| | | |
|---|---|---|
| 4,887,606 A | 12/1989 | Yock et al. |
| 5,080,103 A | 1/1992 | Olivier |
| 5,103,825 A | 4/1992 | Hokanson et al. |
| 5,131,395 A | 7/1992 | Gehlbach |
| 5,167,630 A | 12/1992 | Paul |
| 5,309,915 A | 5/1994 | Ember |
| 5,427,108 A * | 6/1995 | Bollinger .................... 600/461 |
| 6,056,692 A | 5/2000 | Schwartz |
| 6,132,379 A * | 10/2000 | Patacsil et al. ............... 600/459 |
| 6,379,307 B1 | 4/2002 | Filly et al. .................. 600/461 |

* cited by examiner

FIG. 9

# NEEDLE INSERTION SYSTEMS AND METHODS

CROSS-REFERENCE TO RELATED APPLICATION

This application claims the benefit of U.S. provisional application No. 60/489,125 entitled, "A Device For Locating Veins and Aligning and Inserting Intravenous Catheters and Blood Drawing Needles Therein," filed Jul. 22, 2003, which is entirely incorporated herein by reference.

TECHNICAL FIELD

The present disclosure is generally related to the medical field, and, more particularly, is related to systems and methods for locating veins and other blood vessels and inserting needles and catheters therein.

BACKGROUND

In the medical field, a common procedure performed by emergency medical technicians, phlebotimists, nurses, doctors, and other medical field personnel is locating veins and inserting intravenous (IV) tubes (e.g., catheters) and blood drawing needles therein. One problem that is often encountered when administrating an IV or drawing blood is that it is often difficult for the medical person to locate a vein. This problem is particularly pronounced with obese or pediatric patients, or when conditions are less than favorable, for example on a battlefield or at an accident scene. Various methods and devices have been devised to help a user to locate a vein that would be otherwise difficult to locate.

One popular method for locating a vein is the Doppler sonar method. In this method, a transmitter (or transceiver) provides a high frequency sound signal that is transmitted through the surface of a patient's skin in an effort to locate a vein. Although sound will be scattered by all tissues, for the blood flowing through a vein, the signal will be Doppler shifted due to the motion of the blood. If the velocity of the blood is v, the received signal (received at the transducer of a transceiver or receiver) is shifted in frequency as provided in Equation 1 below:

$$\Delta f = 2f \frac{v}{c} \cos\theta \qquad \text{Eq. 1}$$

where f is the transmitted frequency (e.g., 10 Mega-Hertz (MHz)), c is the speed of sound in the tissue (approximately 1500 meters per second (m/sec)) and $\theta$ is the angle between the flow velocity direction and the sound beam axis. For a typical vein, the flow velocity is of the order of 10 cm/sec. If $\theta$ is, for example, 30°, the frequency shift will be 667 Hz. Such shifts can be detected by "beating" the received signal against the transmitted signal. The presence of an audio frequency beat signal in the output (in this case at 667 Hz) indicates a Doppler shift, and hence that the beam is intersecting a blood vessel such as an artery or vein. Since arterial flow is away from the heart and venous flow is towards the heart, the distinction between arteries and veins is made by determining whether the Doppler shift is positive or negative. Both the size of the Doppler shift and the strength of the Doppler shifted signals are helpful in selecting the most suitable vein since a larger vein has higher flow velocities in addition to being a better scatterer.

Although the technology used to locate a vein has improved, the methods used to insert a needle quickly and accurately using a hand-held device and at a moderate cost could benefit from further development.

SUMMARY

Preferred embodiments of needle insertion systems and methods are disclosed. One method embodiment, among others, can be generally described by the following steps: transmitting a sound beam along an axis to contact a blood vessel; receiving the reflected sound beam from the blood vessel; processing the reflected sound beam to detect the location of the blood vessel; and, responsive to the detection, receiving a needle in a guideway that is oriented parallel to the axis.

Another embodiment of a needle insertion method, among others, can generally be described by the following steps: transmitting a sound beam along a first axis to contact a blood vessel; receiving a reflected sound beam reflected from the blood vessel along the first axis; processing the reflected sound beam to detect the location of the blood vessel; and, responsive to the detection, receiving a needle in a guideway that is oriented along a second axis that enables the needle to intersect the first axis in proximity to the blood vessel.

A needle insertion system embodiment, among others, can include a transducer assembly configured to radiate a sound beam along a first axis and detect a blood vessel responsive to receiving a reflected sound beam; and a coupler that is configured to reflect the sound beam along a second axis to and from the blood vessel, the coupler configured with a guideway that is oriented parallel to the second axis.

Another needle insertion system, among others, can include a transducer assembly configured to radiate a sound beam along a first axis and detect a blood vessel responsive to receiving a reflected sound beam; and a coupler that is configured to reflect the sound beam along a second axis to and from the blood vessel, the coupler configured with a guideway that is oriented along a third axis that enables the needle to intersect the second axis in proximity to the blood vessel.

The preferred embodiments also include a coupler that acts as an interface between a needle and a skin surface through which the needle is to advance to contact a blood vessel. In one embodiment, among others, a coupler can include means for receiving a reflected sound beam along a first axis; and means for receiving a needle along an axis that is parallel to the first axis.

Another embodiment of a coupler, among others, can include means for reflecting a transmitted sound beam along a first axis and a reflected sound beam reflected from a blood vessel along the first axis; and means for receiving a needle along a second axis that is oriented to enable the needle to intersect the first axis in proximity to a blood vessel in which the needle is to be inserted.

Other systems, methods, features, and advantages of the disclosure will be or become apparent to one with skill in the art upon examination of the following drawings and detailed description. It is intended that all such additional systems, methods, features, and advantages be included within this description, and be within the scope of the disclosure.

BRIEF DESCRIPTION OF THE DRAWINGS

The components in the drawings are not necessarily to scale, emphasis instead being placed upon clearly illustrating the principles of the disclosed systems and methods. Moreover, in the drawings, like reference numerals designate corresponding parts throughout the several views.

DETAILED DESCRIPTION OF THE PREFERRED EMBODIMENTS

Disclosed herein are various embodiments of a needle insertion system and method. A needle insertion system assists a user (e.g., a skilled medical professional such as a nurse, or an unskilled person for do-it-yourself medical kits) in locating a vein, for example, or artery, and inserting an intravenous (IV) tube, catheter, and/or blood drawing needle therein. In one embodiment, a needle insertion system is disclosed as comprising a handheld device having a transducer assembly and a coupler. The transducer assembly includes a focused ultrasonic transducer that produces a narrow sound beam with a focal region (e.g., the focal region in one embodiment having a diameter of less than or equal to approximately 1 millimeter (mm), approximately 2.5 centimeters (cm) in length, and whose center is approximately located 5 cm from the transducer face). The sound beam is preferably generated as a pulsed beam having a frequency of approximately 10 Mega-Hertz (MHz). The transducer, operating in one embodiment in a transmit/receive mode, detects a vein by functioning as a pulsed Doppler blood flow detector.

The coupler is configured to guide or direct a needle into a vein quickly and easily, and, preferably, to detach from the needle quickly and easily. In principle, the coupler portion works by aligning the axis of a needle relative to the axis of the sound beam radiated from the transducer assembly. If the beam is known to intersect a vein (using Doppler sonar), then advancing the needle in a path provided integral to or adjacent to the coupler along the beam axis, parallel to the beam axis at a slight offset, or offset in a depth dependent manner to intersect the beam axis, results in the needle entering the vein.

Although described in the context of locating a vein and inserting a needle therein, it would be understood by those having ordinary skill in the art that the principles disclosed in this disclosure can also apply to the location of other blood-carrying vessels.

Further, although described using a needle, similar principles apply to the insertion of other objects such as a catheter, tube, or shunt, and thus are considered to be within the scope of the preferred embodiments.

Figure 1:
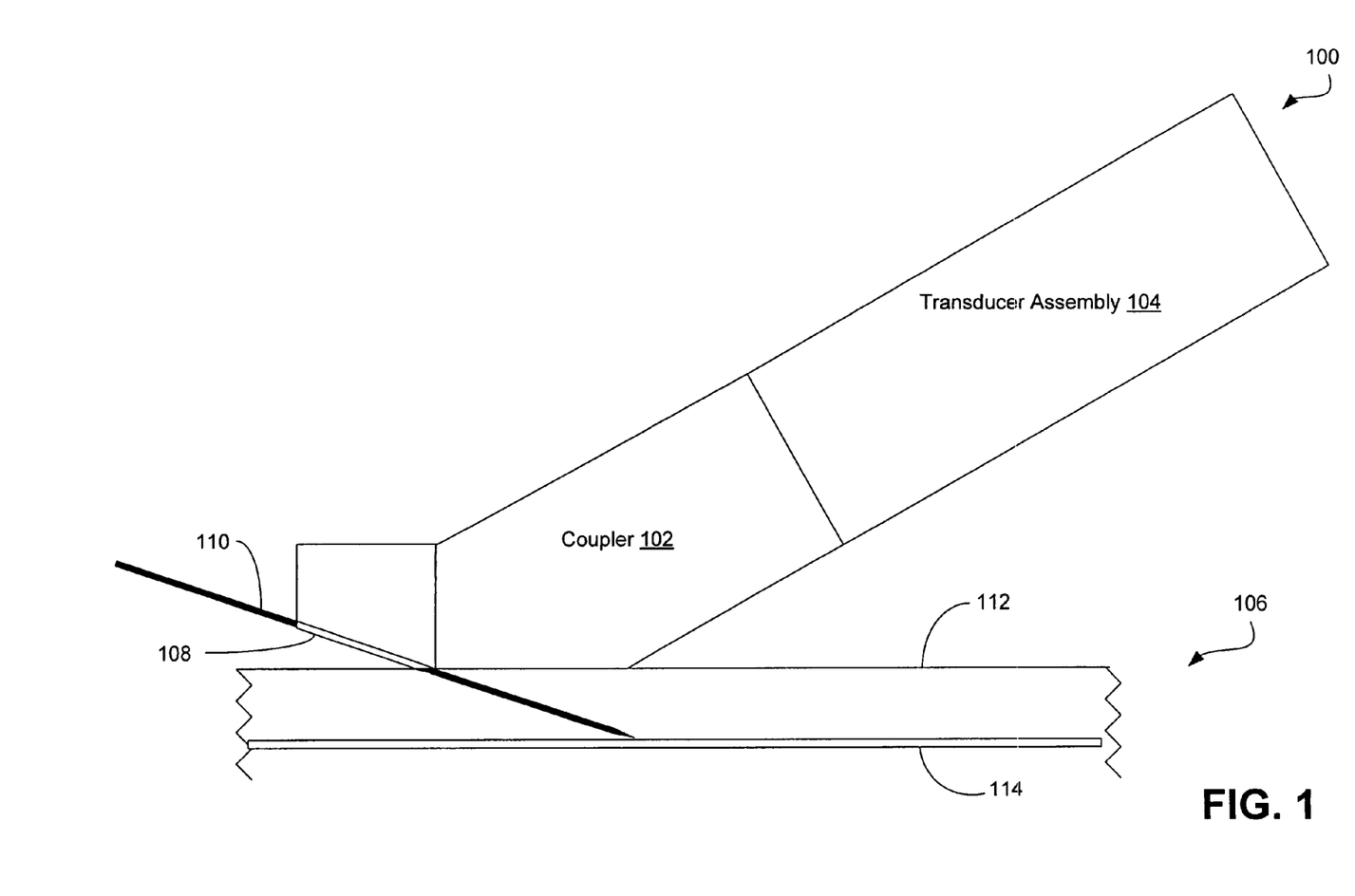
FIG. 1 is a schematic diagram that illustrates an embodiment of a needle insertion system.
Figure 2:
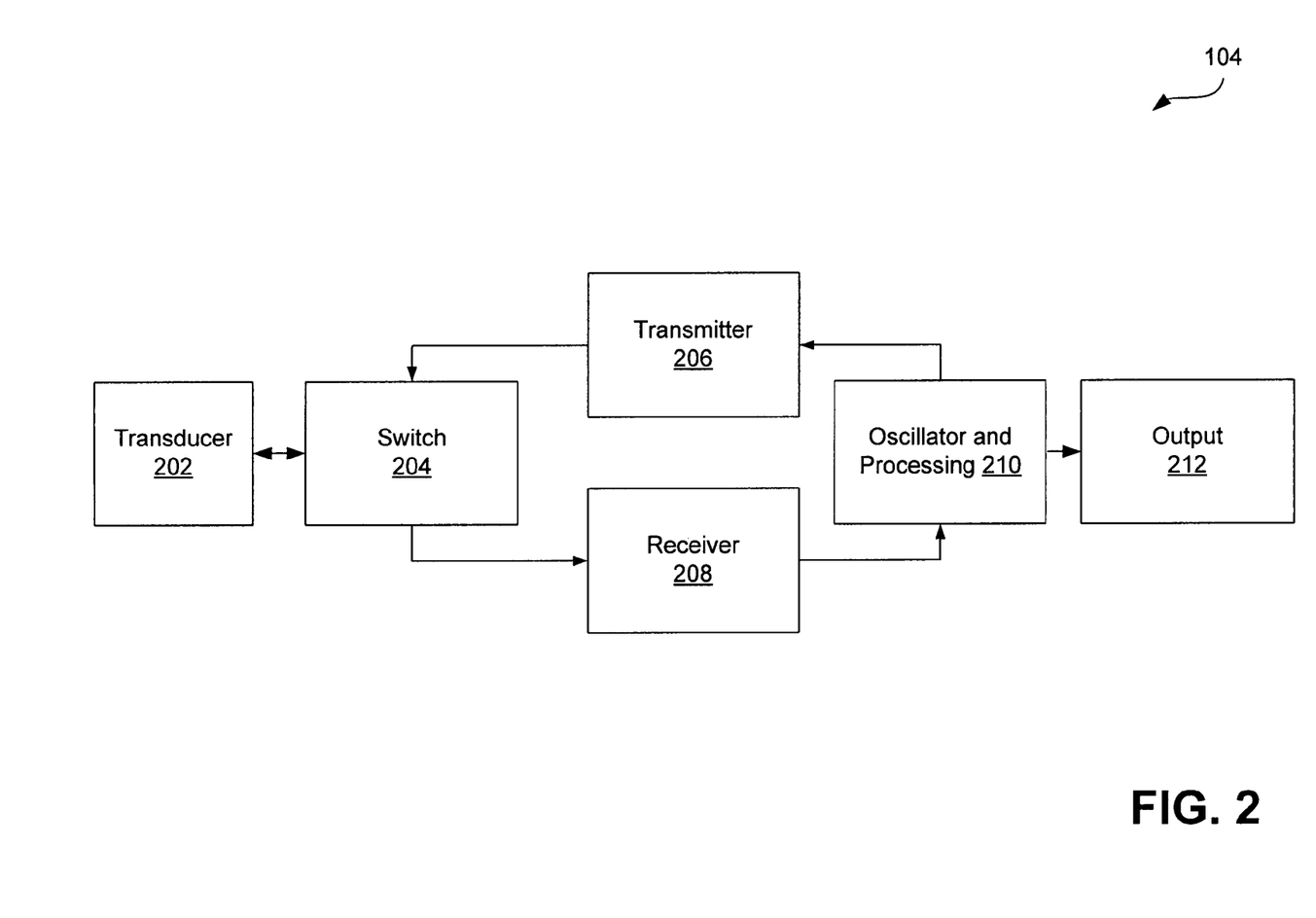
FIG. 2 is a block diagram that illustrates an embodiment of a transducer assembly of the needle insertion system shown in FIG. 1.
Figure 3:
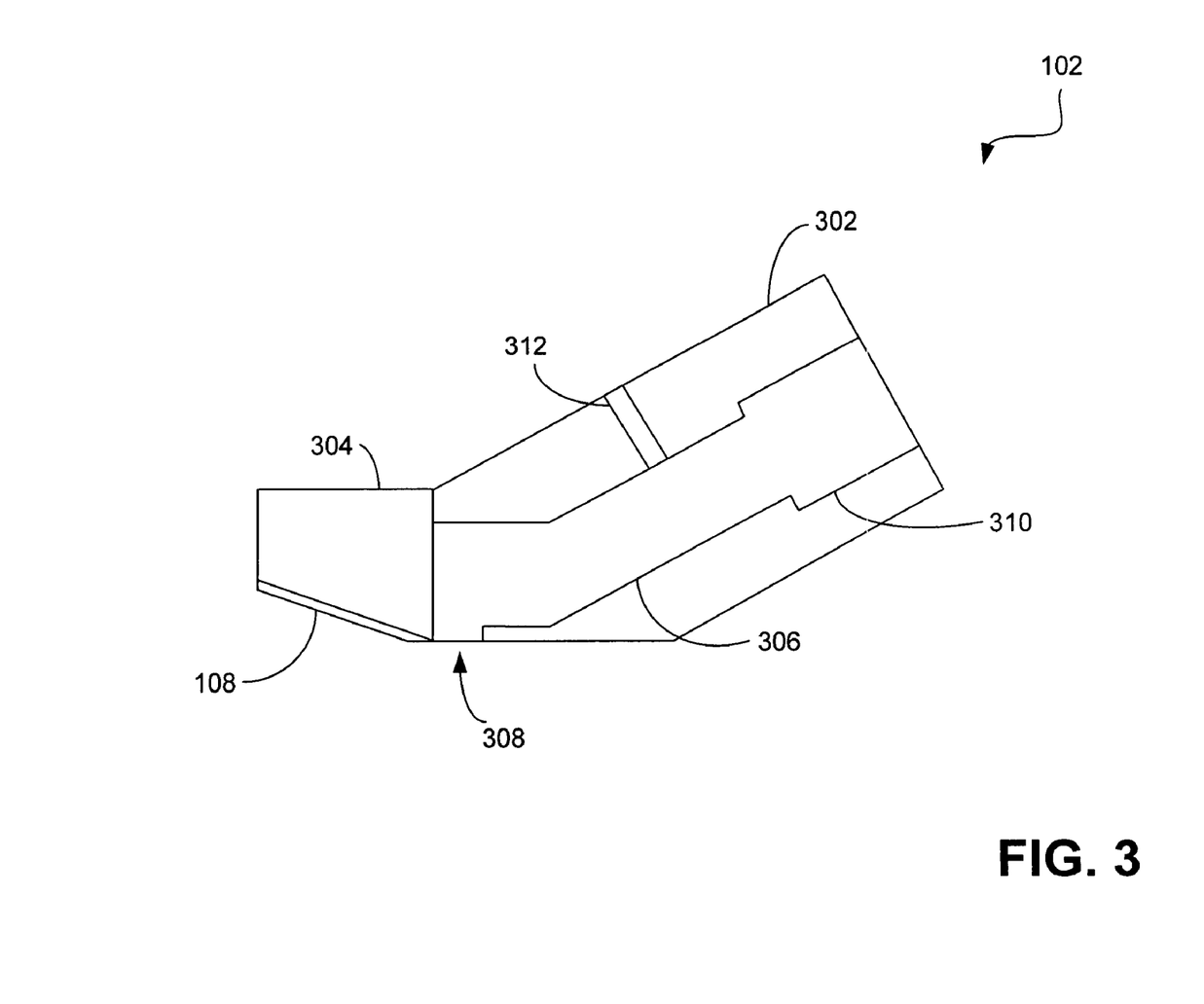
FIG. 3 is a side-view cut-away that illustrates an embodiment of a coupler of the needle insertion system shown in FIG. 1.
Figure 4:
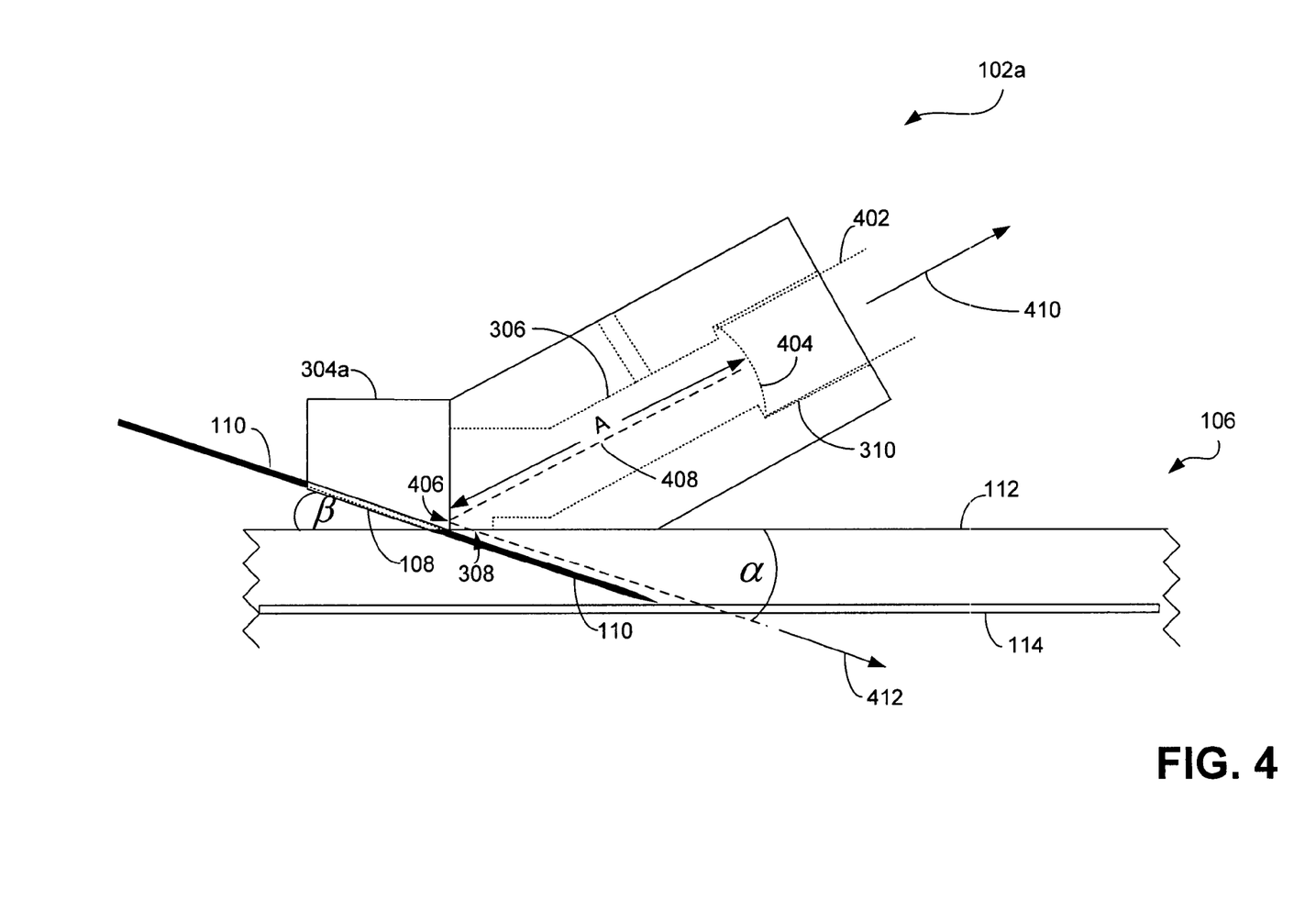
FIG. 4 is a schematic diagram of a coupler embodiment similar to that shown in FIG. 3 that illustrates application of a sound beam and receiving a needle along an axis that is parallel to and offset from a sound beam axis.
Figure 5:
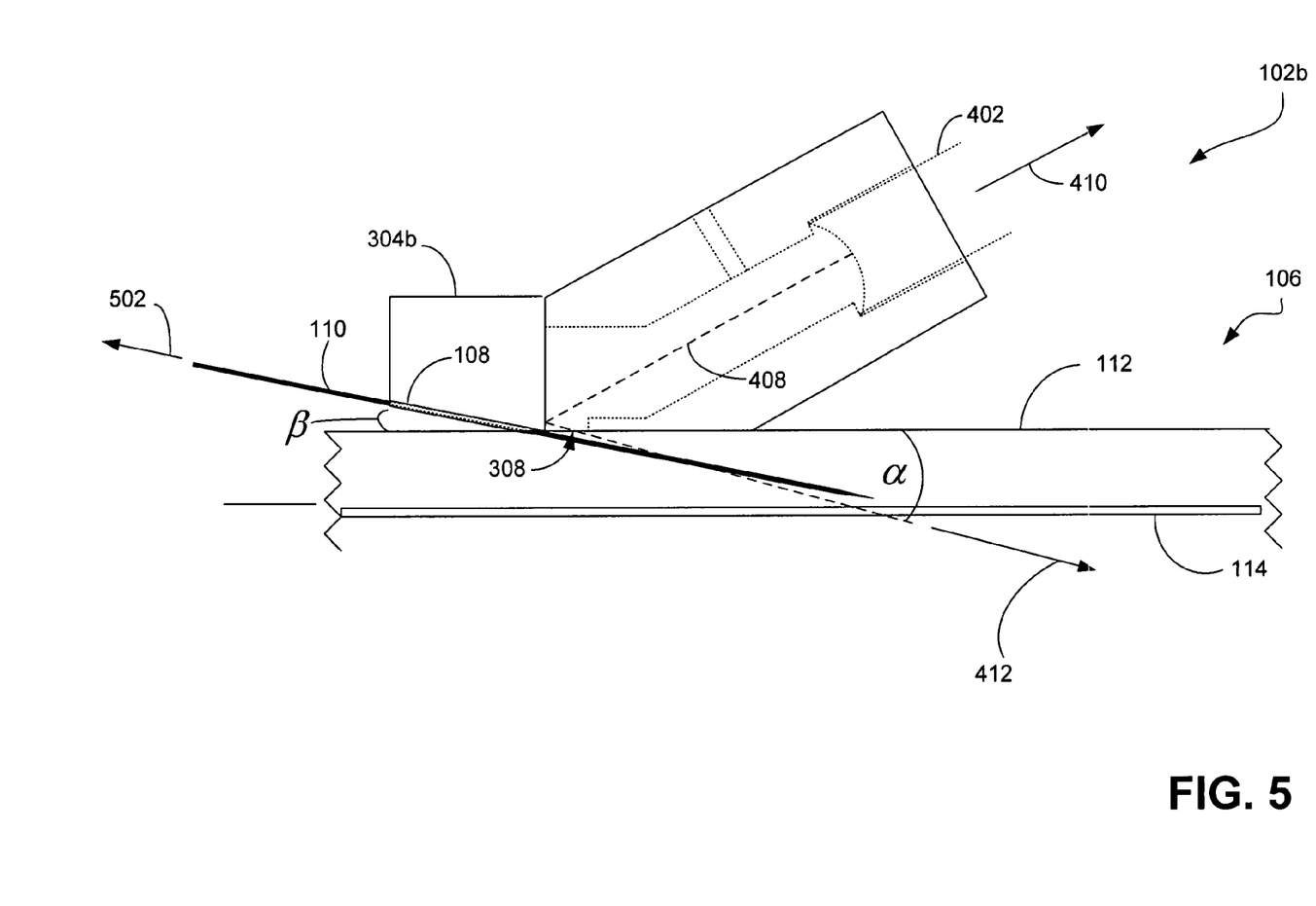
FIG. 5 is a schematic diagram of another coupler embodiment similar to that shown in FIG. 3 that illustrates application of a sound beam and receiving a needle along an axis that has a depth dependent offset relative to a sound beam axis.
Figure 6:
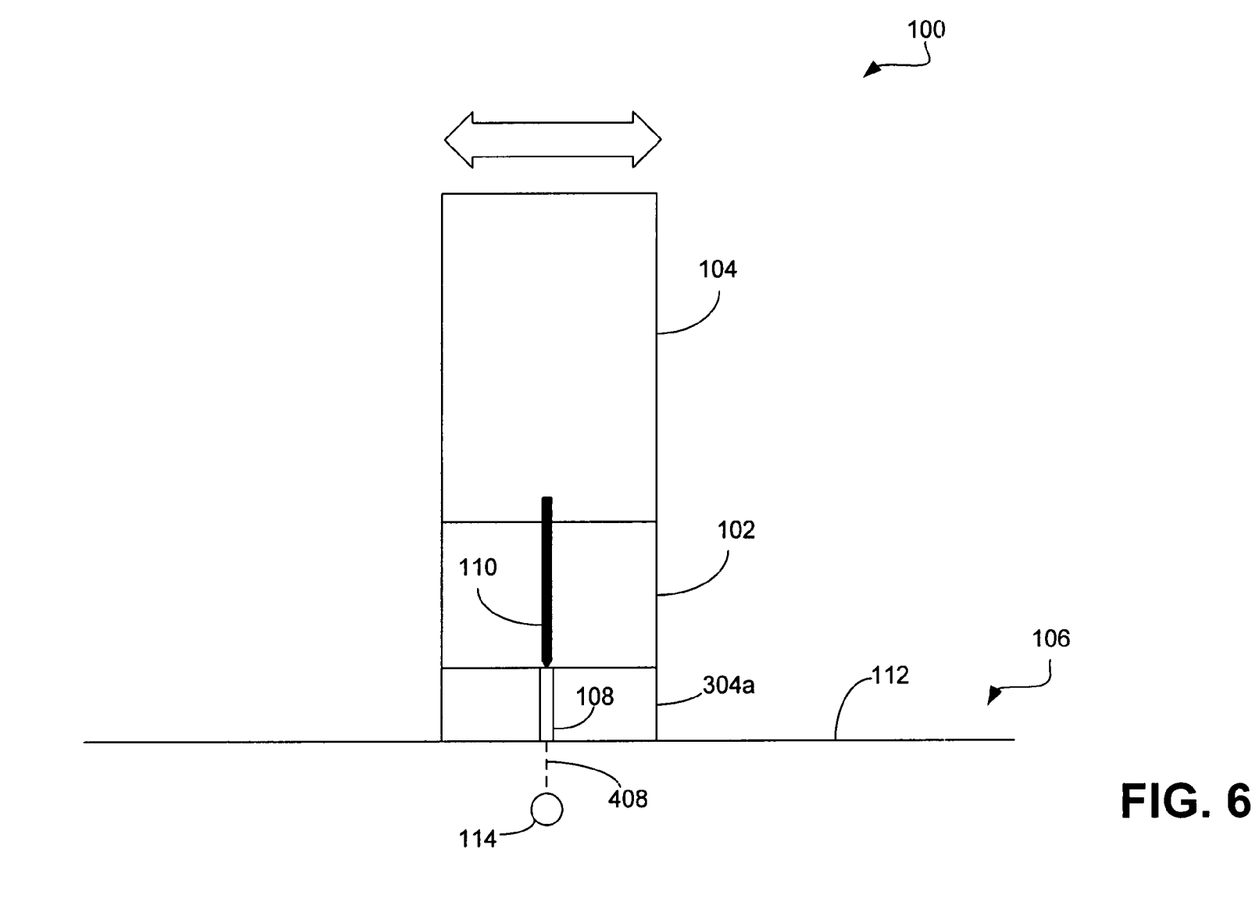
FIG. 6 is a front-view schematic diagram of the needle insertion system shown in FIG. 1 that illustrates traversing the skin surface to obtain a strong signal that indicates location of a suitable vein and insertion location along the vein.
Figure 7A:
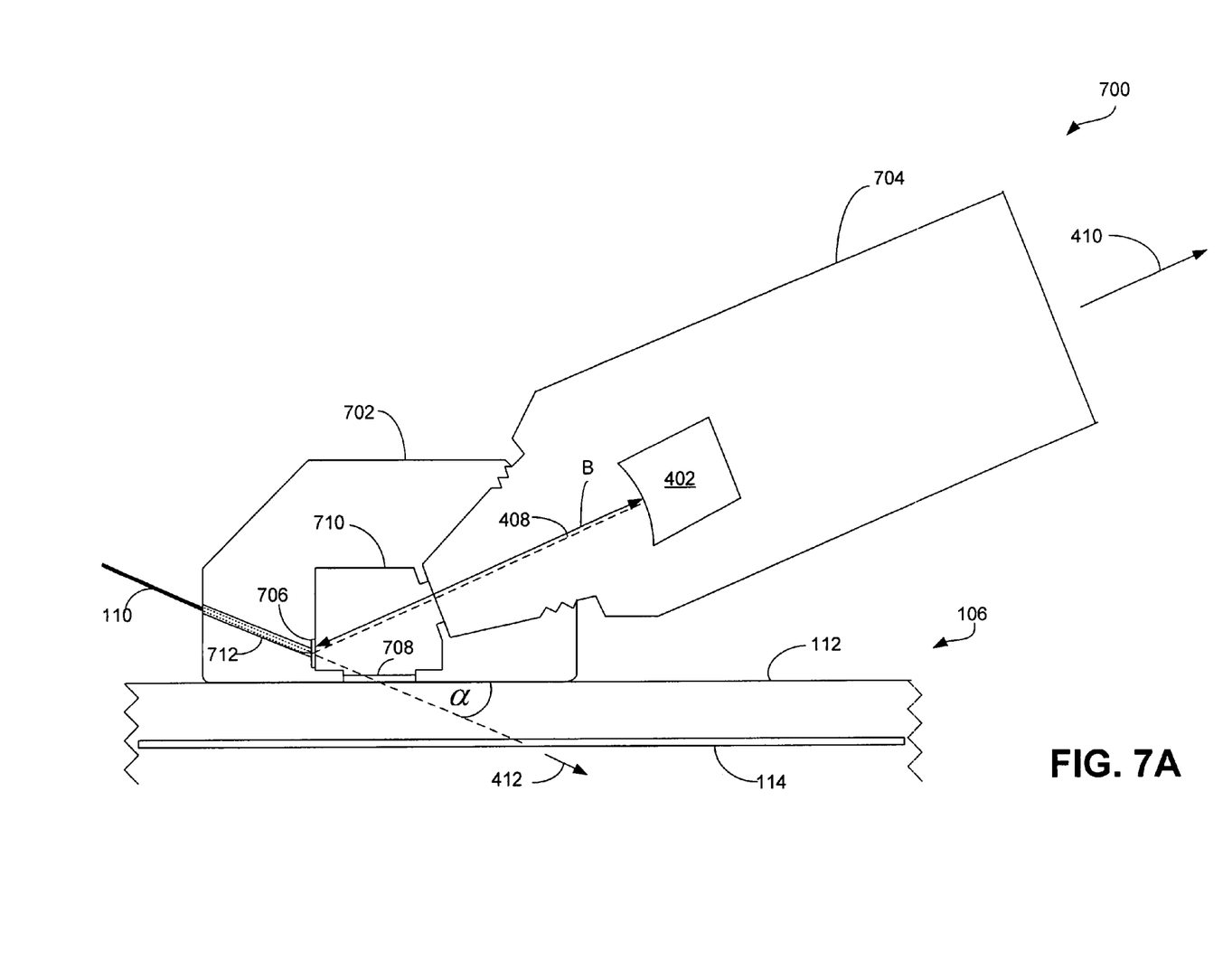
FIG. 7A is a schematic diagram that illustrates an embodiment of a needle insertion system.
Figure 7B:
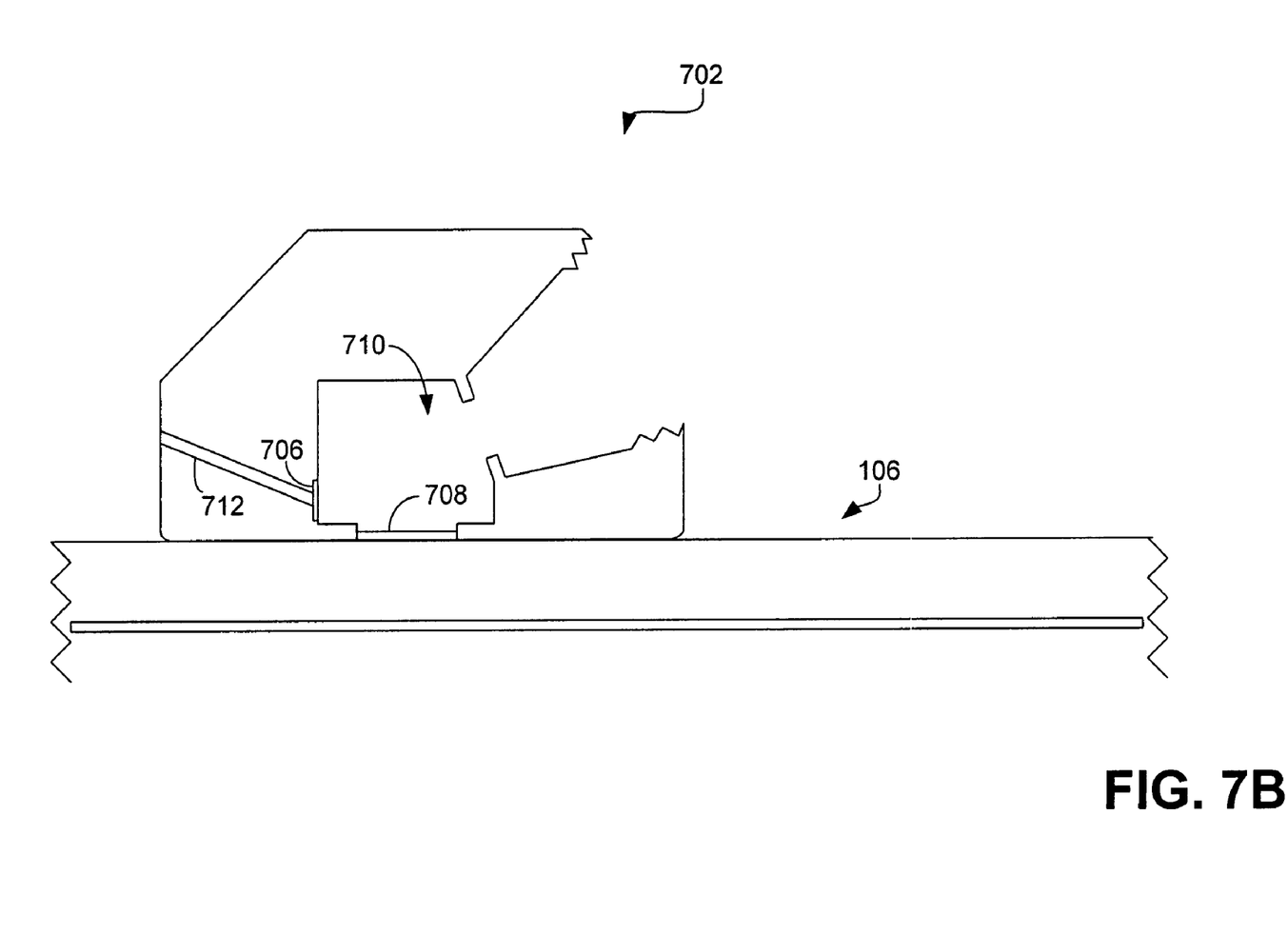
FIG. 7B is a side-view cut-away of an embodiment of a coupler of the needle insertion system shown in FIG. 7A.
Figure 8:
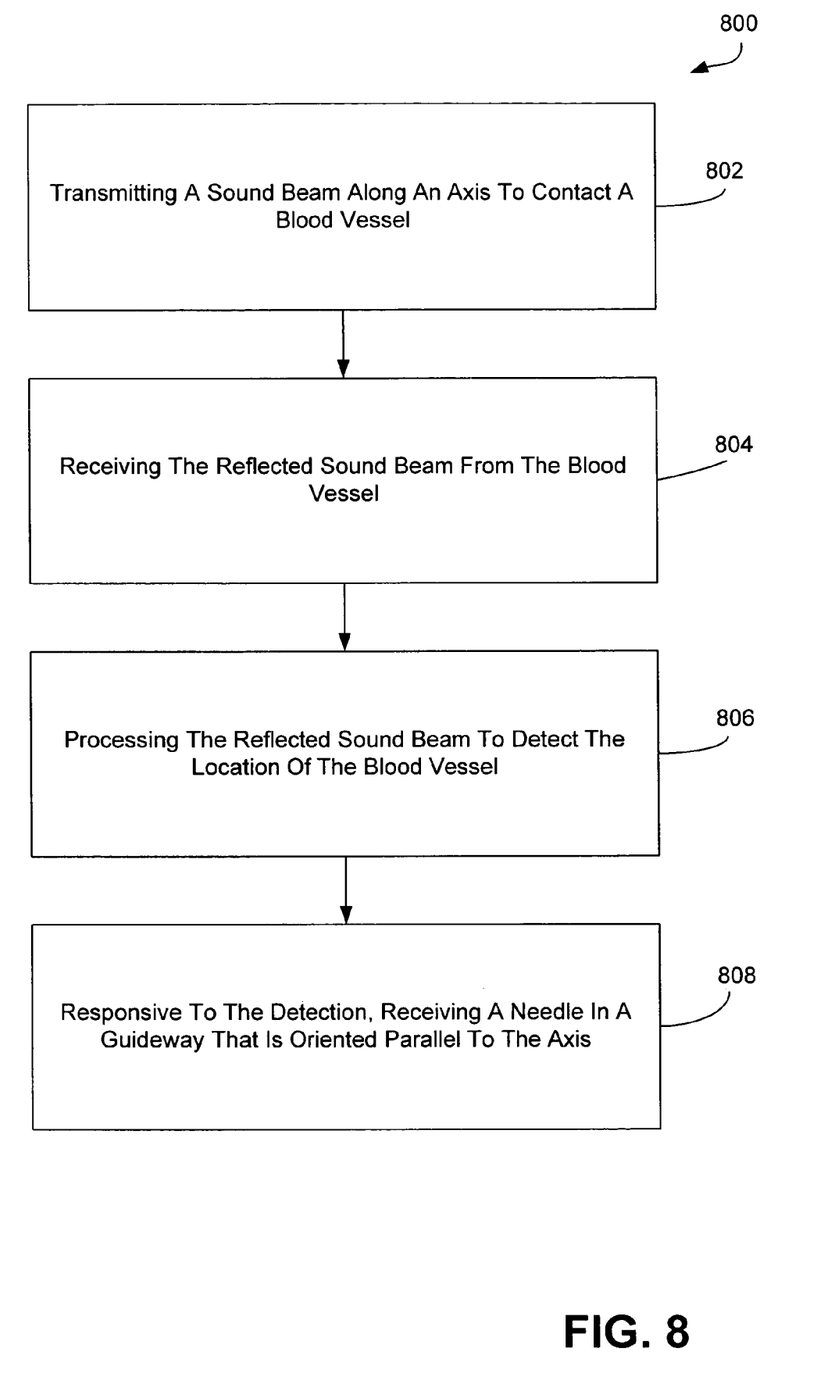
FIG. 8 is a flow diagram that illustrates one needle insertion method embodiment corresponding to the embodiment shown in FIG. 4.
Figure 9:
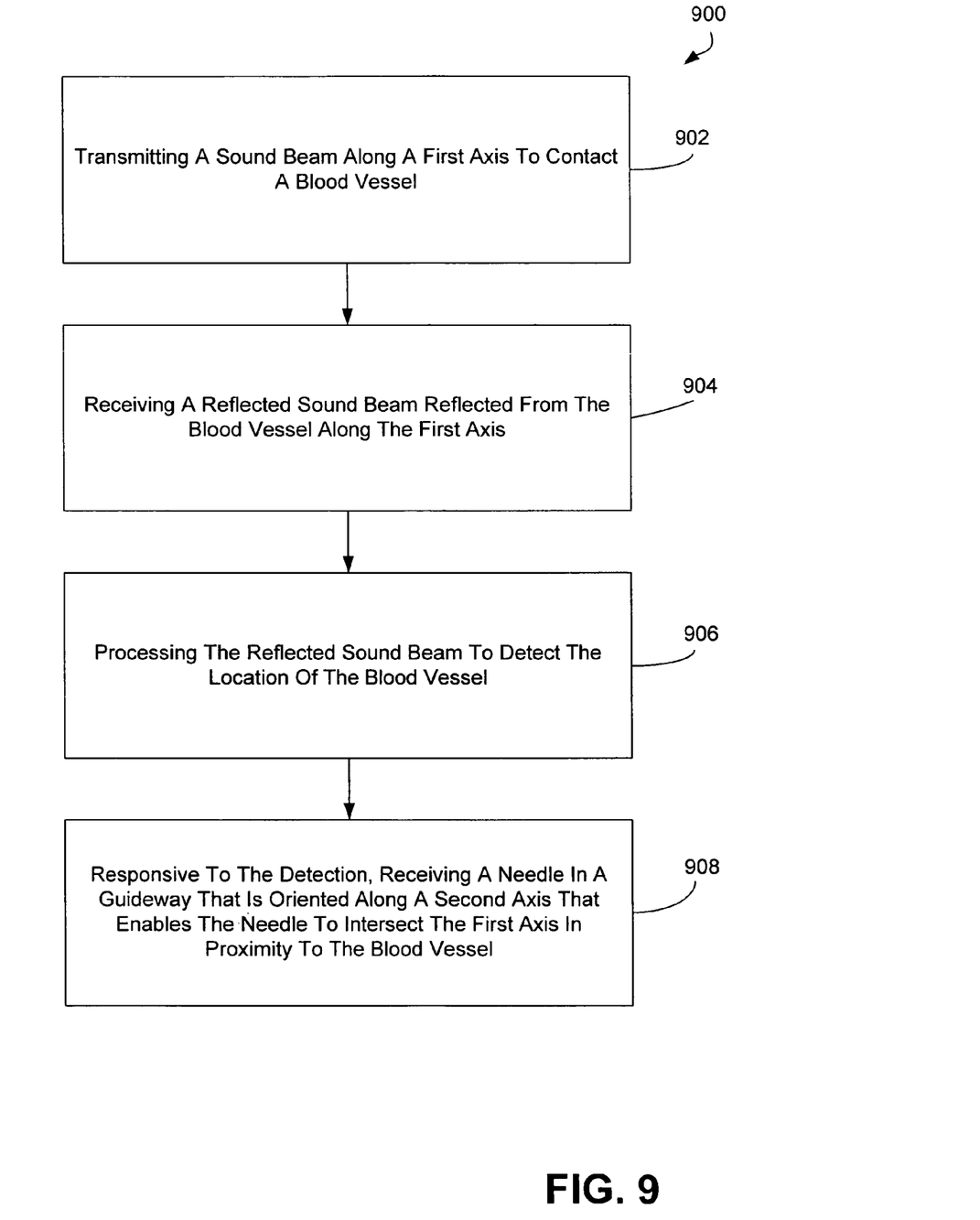
FIG. 9 is a flow diagram that illustrates one needle insertion method embodiment corresponding to the embodiment shown in FIG. 5.

In the description that follows, a needle insertion system embodiment is described in FIG. 1, and the various components that comprise the same is described with respect to FIGS. 2-4. An additional embodiment of a coupler for the needle insertion system described in FIG. 1 is illustrated in FIG. 5. FIG. 6 illustrates a method to elicit an optimal feedback signal indicating whether or when the center of a vein has been located. FIGS. 7A and 7B illustrate another embodiment of a needle insertion system and its corresponding components. Finally, FIGS. 8 and 9 illustrates various needle insertion method embodiments.

FIG. 1 is a schematic diagram that illustrates an embodiment of a needle insertion system. The needle insertion system 100 includes a coupler 102 and a transducer assembly 104. The coupler 102 includes a guideway 108, in which a needle 110 can be inserted and advanced along the guideway 108 and through the skin surface 112 to puncture a vein 114 located in a body 106 (for blood drawing and catheter insertion, the body site of interest will often be an arm, but the needle insertion system can be used in other locations of the body). Although the guideway 108 can be configured as a channel that runs through the body of the coupler 102, preferably the guideway 108 is configured as a channel that runs along the bottom, preferably angled surface of the coupler 102. The transducer assembly 104 can be rotatably attached and detached from the coupler 102, and/or slidably detached and re-attached in other embodiments according to well-known attachment/detachment mechanisms. Still in other embodiments, the transducer assembly 104 and the coupler 102 can be fixably attached or the two components can be molded as a single component. The needle 110 can be packaged with the coupler 102, for example disposed in the guideway 108 as part of the entire coupler 102, or available separately from the coupler 102.

FIG. 2 is a block diagram that illustrates an embodiment of a transducer assembly 104 of the needle insertion system 100 shown in FIG. 1. The transducer assembly 104 includes a transducer module 202, a switch module 204, a transmitter module 206, a receiver module 208, an oscillator and processing module 210, and an output module 212. One or more of the modules can be configured in hardware, software, or a combination of hardware and software. The transducer assembly 104 can be battery powered (not shown) and/or powered externally through use of a cord or other mechanism for connecting to an external power source.

The transducer module 202 preferably radiates a pulsed Doppler sound field which, in one embodiment, focuses to a beam of approximately 1 mm in diameter over a length of approximately 2.5 cm, as generated from the transmit electronics described below. The 1 mm diameter sound beam is smaller or comparable in diameter to a vein from which it is suitable to draw blood. The transducer module 202 includes a transducer element (not shown) that can be configured to radiate beams of greater or smaller diameter depending on the application, by adjusting the frequency. The transducer module 202 is also configured to receive a reflected sound beam, which it converts to a signal(s) for processing by the receive electronics described below.

The oscillator and processing module 210, in cooperation with the transmitter module 206, generate the pulses at a frequency of approximately 10 MHz, although sound beams of other frequencies can be generated depending on the application. The pulsed mode is preferably implemented in both transmit and receive modes. The receiver module 208 includes receive and processing electronics to receive the reflected signal and determine the presence or absence of a Doppler shift. If a Doppler shift is detected, an audible sound, tactile sensation (e.g., vibration), and/or visual display is activated via the output module 212. For example, an audible sound may be activated and may be adjustable based on the surrounding environment (e.g., loud enough to hear over sirens, etc.). As another example, a graphics user interface may be presented on the package of the transducer assembly 104 and which may show an arrow(s) indicating the direction of movement a user needs to take along a person's body to locate a vein or to optimize the signal strength (and thus center the needle on the vein). The switch module 204 provides functionality for switching between receive and transmit functionality. Note that the use of pulsed Doppler may also enable estimation of the depth of the vein from the pulse transit time. Further, the electronics of the transducer assembly 104 are well known to those having ordinary skill in the art, and thus further explanation of each component will be omitted for brevity.

The transducer assembly 104, when detachable from the coupler 102, does not have to be sterilizable. As a corollary to the detachable/attachable feature, the transducer assembly 104 is reusable with a plurality of different couplers 102.

Note that in some embodiments, two transducers may be used (a transmit and receive transducer) and the switch omitted.

FIG. 3 is a side-view cut-away that illustrates an embodiment of a coupler of the needle insertion system 100 shown in FIG. 1. The coupler 102 comprises a coupling portion 302 and a reflective portion 304. In one embodiment, the coupler 102 may be disposable, and included with the needle 110 in a plastic package (not shown) designed to maintain the sterility of the coupler 102 and the needle 110. The coupling portion 302 is preferably made of a plastic material, although other materials may be used. The coupling portion 302 comprises a chamber 306 that is preferably cylindrical in configuration. The chamber 306 contains a coupling material (not shown). The coupling material may include water, ultrasonic gel, solid rubber couplant, among other coupling material suitable for propagating the sound beam. The coupling portion 302 also includes a window 308 which allows the transmitted sound beam to radiate into the body 106 (FIG. 1) and allows the reflected sound beam to radiate back into the coupling portion 302. The window 308 may be comprised of a thin (e.g., approximately 25 microns to 250 microns thick) plastic material. The coupling portion 302 further includes a housing portion 310, which receives a transducer element (not shown) of the transducer module 202 (FIG. 2) when the coupling portion 302 is attached to the transducer assembly 104. The coupling portion also include a tube 312. The tube 312 serves as a conduit to enable filling the coupler with a coupling material, such as water. In some implementations, an ultrasonic coupling gel (not shown) may be applied to the outside surface of the coupler 102 (i.e., the surface contacting the skin surface 112).

The reflective portion 304 is attached to the coupling portion 302, for example using an adhesive, through the use of screws, or other fastening mechanisms known to those having ordinary skill in the art. The reflective portion 304 preferably has a flat reflecting surface (reflecting the sound beam) and is preferably comprised of a metallic material, such as stainless steel, although other reflective material, or a combination of reflective and non-reflective material, may be used. The reflective portion 304 redirects the sound beam received from a transducer element, or the reflected sound beam received from the located vein, at a defined angle. The reflective portion includes a guideway 108 that has a defined angle with respect to the skin surface 112 (FIG. 1), and is used to guide a needle along a predetermined orientation. In one embodiment, the guideway 108 is configured to provide a predetermined offset between the sound beam and the needle. The offset can be made depth-dependent or depth-independent by modifying the attachment angle (i.e., the angle between the guideway 108 and the horizontal surface of the coupler 102, such as $\beta$ in FIG. 4 described below) with respect to the skin surface 112.

In one embodiment, the guideway 108 is made of a short, flexible tube attached to (adjacent) the reflective portion 304 (e.g., running along the bottom, angled surface of the reflective portion 304). The guideway 108 is preferably made of a plastic material, and can be attached using an adhesive or other fastening mechanisms known to those having ordinary skill in the art. A slot (not shown) is provided at the bottom of the guideway 108 running along the length of the guideway to enable a user to disengage the coupler 102 from a needle once the vein is punctured. In some embodiments, the slot can be omitted and the coupler 102 can be disengaged from the needle by cutting the guideway 108. In some embodiments, the slot can be omitted based on applications where disengagement from the needle is not needed. The guideway 108 has a diameter that is large enough to allow the needle to be advanced through it, yet small enough to hold the needle firmly. In some embodiment, a guideway of similar features can be configured as a channel bored within the body of the reflective portion 304.

FIG. 4 is a schematic diagram of a coupler embodiment, coupler 102a, similar to that shown in FIG. 3, and that illustrates application of a sound beam and receiving a needle along an axis that is parallel to and offset from a sound beam axis. As shown, a transducer element 402 of the transducer assembly 104 (FIG. 1) is disposed conformably (although any well-known attachment/detachment mechanisms may be employed) in the housing portion 310 and secured enough to assure proper alignment between the transducer assembly 104 and the coupler 102a. In one embodiment, the transducer element 402 has a concave surface 404 to provide a focused sound beam. The focused beam could also be achieved using an acoustic lens. The transducer element 402 is disposed at a distance (represented by the line labeled "A" in FIG. 4) of approximately 4 cm from the location 406 on the reflective surface on which a sound beam 408 (shown herein as the centerline of the beam, with the understanding that a larger sound profile is preferably radiated) impinges to the point on the convex surface 404 farthest from said location 406. This 4 cm distance enables a 1 mm diameter sound beam focal region to begin at the skin surface. Note that this dimension "A" may vary in some embodiments, depending on the characteristics of the sound beam from the focused transducer element 402. "A" can be determined mathematically according to known formulas, and/or determined (or verified) experimentally. Thus, the transducer element 402 is disposed in the housing portion 310 at a suitable distance to accommodate a focal length of approximately 5 cm, in such a way that the focal region begins at the surface of the skin 112, which enables detection of a vein along a longer range. For example, experimentation and mathematical analysis have indicated that the focal region for a sound field produced by a 1 centimeter (cm) diameter, 10 MHz transducer with a focal length of 5 cm is ellipsoidal, about 1 mm in diameter, and more than 2 cm long. In other words, there exists a "beam-like" quality of the sound field within ±1 cm of the focal point.

The sound beam 408 is radiated in the chamber 306 along an axis that is coincident with a first axis 410. The chamber 306 includes a coupling material (not shown) that provides an appropriate low loss impedance matched propagation medium for the sound beam 408 when entering the interior of the body 106 and returning from the interior of the body 106.

The sound beam 408 impinges on the reflective portion 304a at location 406 and is reflected along an axis coincident with a second axis 412. In one embodiment, the angle α between the reflected sound beam along the second axis 412 and the skin surface 112 is approximately 30°, although other angles may be used. The reflected sound beam 408 is transmitted through the skin surface 112 and impinges on the vein 114, and then at least a portion of the beam is reflected back to the transducer element 402 along the second axis 412, and then the first axis 410 after reflection at 406 of the reflective portion 304a. The transducer element 402 converts the received sound beam 408 to an electronic signal that is processed in the receive electronics (e.g., 208, 210 of FIG. 2) of the transducer assembly 104 to elicit a feedback response by the output module 212 (FIG. 2). A feedback response provides an indication that a vein has been located, and in some embodiments, an indication of the signal strength corresponding to whether the vein has been located at a position offset from the centerline of the vein (where blood flow may be slower) or at the centerline (where blood flow is greatest).

If the vein 114 is located and the signal strength indicates that the location corresponds to an optimal position for insertion of the needle 110, then the user can insert the needle 110 through the guideway 108. The guideway 108 is oriented parallel to the second axis 412, offset a fixed and constant distance (e.g., 0 to 5 mm) from the second axis 412. By remaining offset from the second axis 412, the inserted needle 110 interferes minimally with the sound field present beneath the skin surface 112, and enables the user to continually monitor the location of the vein 114 as the needle is advanced, up until the time corresponding to when the vein 114 is punctured. In one embodiment, the angle β which is the angle formed between the guideway 108 and the skin surface 112, is approximately 30°, although other angles may be used.

FIG. 5 is a schematic diagram of another coupler embodiment, coupler 102b, that illustrates application of the sound beam 408 and receiving the needle 110 along an axis 502 that has a depth dependent offset relative to a sound beam axis 412. As shown, the coupler 102b has similar components to those found in couplers 102, 102a of FIGS. 3 and 4, respectively, and thus discussion of the same will be omitted or abbreviated. The sound beam 408 is radiated from the transducer element 402 along the first axis 410, reflected off a reflective portion 304b, and provided along the second axis 412 to impinge on the vein 114. The angle α is approximately 30°, although other angles may be used. The guideway 108 (and also the bottom surface of the reflective portion 304b in one embodiment) form an angle β of approximately 23°, although other angles may be used. Thus, the needle 110 is advanced along the guideway 108 along a third axis 502, resulting in the needle 110 intersecting the sound beam 408 provided along the second axis 412 in a location proximally (i.e., the axis 502 intersecting axis 402 in a location approximately at the point where the focal region ends, such as where the beam width ceases to be 1 mm in diameter in embodiments described herein) to the vein 114. Note that the offset will vary based on the depth of the vein 114.

FIG. 6 is a front-view schematic diagram of the needle insertion system 100 shown in FIG. 1 that illustrates traversing the skin surface 112 to obtain a strong signal indicating location of the vein 114 and/or optimal locations along the vein 114. For example, the needle insertion system 100 is shown traversing across the skin surface, but it also is traversable in the direction running along the length of the body 106, as well as rotatably traversable. In one implementation, the needle insertion system 100 is moved (represented by the double-arrow head above the system 100) across the skin surface 112 until the vein 114 is detected. Vein detection (and/or location) may be indicated by a light, sound or other display or feedback, as described above. The sound beam reflection from the vein 114 enables the needle 110 (or an IV catheter, for example, in some implementations) to be aligned, but offset, with the sound beam 408. In other words, the sound beam 408 is known (using Doppler technology) to be passing through a suitable vein 114. The needle is advanced through the guideway 108a (parallel to, but offset from the sound beam 408 in this implementation), passing through the skin surface 112 and advanced until it punctures the vein 114. The user continually receives feedback that he or she is advancing the needle 110 in the right direction until the vein 114 is punctured.

FIG. 7A is a schematic diagram that illustrates another embodiment of a needle insertion system 700. The needle insertion system 700 differs from the prior described embodiments in that a needle is advanced to a vein along an axis that is coincident with the sound beam. The needle insertion system 700 includes a transducer assembly 704 attached to the coupler 702. Preferably, the transducer 704 is attachable and detachable from the coupler 702 (e.g., shown here as rotatably attachable and detachable). The transducer assembly 704 includes the same or similar electronics to the transducer assembly 104 shown in FIG. 2, and thus illustration and discussion of the same is omitted.

FIG. 7B is a side-view cut-away of an embodiment of the coupler 702 of the needle insertion system 700 shown in FIG. 7A. With continued reference to FIG. 7A, the coupler 702 is preferably made of plastic, and comprises membranes 706 and 708 and a chamber 710 that includes an ultrasonic coupling material (not shown). Membranes 706 and 708 may be made of, for example, rubber. The coupling material can be, for example, a sterile, de-aerated saline. In one embodiment, the coupler 702 may be disposable, and included with the needle 110 in a plastic package (not shown) designed to maintain the sterility of the coupler 702 and the needle 110. For IV catherization implementations, the coupler 702 can be designed to split in half to allow removal of the coupler 702 after the vein 110 has been punctured, an unnecessary step for simply drawing blood. The membranes 706 and 708 are traversed by the needle 110 during the insertion, the needle 110 being advanced through the guideway 712. The membrane 706 is also an ultrasound reflector. In one embodiment, the membrane 706 is air-backed and preferably as smooth and flat as possible. The membrane 708 serves to couple the sound beam 408 into the tissue of the body 106. In some implementations, an ultrasonic coupling gel (not shown) may be applied to the outside surface of the membrane 708 (i.e., the surface contacting the skin surface 112).

Directing attention to FIG. 7A, the operation of the transducer system 700 will now be described. The transducer element 402 of the transducer assembly 704 radiates the sound beam 408 a distance (represented by the line labeled "B") of approximately 4 cm to the membrane 706 in similar manner to that described in association with FIG. 4. The sound beam is radiated along a first axis 410. The sound beam 408 is reflected by the air-backed membrane 706 before entering the body 106 through the membrane 708. The reflected sound beam 408 travels along the second axis 412. The travel path and orientation of the reflected sound beam 408 enables the needle 110 (or an IV catheter) to be exactly aligned or substantially aligned with the reflected sound beam 408, which is known by Doppler to be passing through a suitable vein 114. Although the sound beam 408 is shown to make an angle α of 30° relative to the plane of the skin surface 112, it would be understood by one having ordinary skill in the art that some embodiments may utilize one of a variety of different angles (e.g., 45° or 20°) depending on the application.

The needle 110 is advanced (not shown) through the guideway 712, which is coincident (or coaxial) with the sound beam 408. The needle 110 is advanced through the membrane 706, through the chamber 710 (and thus through a coupling material not shown, such as saline fluid), and then through the membrane 708, and continually (still along the second axis 412) advanced until the needle 110 punctures the vein 114. The coaxial alignment of the guideway 712 and sound beam assures (or assures with a high-probability of certainty) that the needle 110 will encounter the vein 114. The coupler 702, in one embodiment, can then be easily disassembled into two or more pieces and removed, and the IV cauterization or blood draw can be completed.

In some embodiments, the saline filled chamber 710 can be replaced with a solid insert (not shown), which can be removed after the vein 114 is detected to allow passage of the needle 110. In such embodiments, the membranes 706 and 708 may be omitted and the user can view the insertion point.

In view of the above description, it will be appreciated that one embodiment of a needle insertion method 800 may comprise, as illustrated in FIG. 8, transmitting a sound beam along an axis to contact a blood vessel (802); receiving the reflected sound beam from the blood vessel (804); processing the reflected sound beam to detect the location of the blood vessel (806); and, responsive to the detection, receiving a needle in a guideway that is oriented parallel to the axis (808).

Another embodiment of a needle insertion method 900 may comprise, as illustrated in FIG. 9, transmitting a sound beam along a first axis to contact a blood vessel (902); receiving a reflected sound beam reflected from the blood vessel along the first axis (904); processing the reflected sound beam to detect the location of the blood vessel (906); and, responsive to the detection, receiving a needle in a guideway that is oriented along a second axis that enables the needle to intersect the first axis in proximity to the blood vessel (908).

Any process descriptions or blocks in the flow diagrams of FIGS. 8 and 9 should be understood as representing steps in an embodiment of one method, and alternate implementations are included within the scope of the preferred embodiments, as would be understood by those reasonably skilled in the art.

It should be emphasized that the above-described embodiments, particularly, any "preferred" embodiments, are merely possible examples of implementations, and are merely set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure.

What is claimed:

1. A needle insertion system, comprising:
a transducer assembly configured to radiate a sound beam along a first axis and detect a blood vessel responsive to receiving a Doppler-shifted reflected sound beam, the focal region of the sound beam being comparable in diameter to or smaller than the blood vessel; and
a coupler that is configured to reflect the sound beam along a second axis to and from the blood vessel, the coupler configured with a guideway that is oriented parallel to the second axis and offset a fixed distance from the second axis, wherein the guideway is receptive to a needle that can be advanced in a direction oriented parallel to the second axis to contact the blood vessel in a location that is proximal to where the sound beam is reflected from the blood vessel.

2. The system of claim 1, wherein the transducer assembly includes at least one of a switch, transmitter electronics, receiver electronics, an oscillator, a power amplifier, a pulse generator, and a processor.

3. The system of claim 1, wherein the transducer assembly includes a transducer set back a defined distance from a point at which the sound beam is reflected along the second axis by the coupler, the transducer configured to radiate a pulsed ultrasonic beam.

4. The system of claim 1, wherein the transducer assembly includes an output module that is configured to provide at least one of an audible sound, a visual display signal, and a tactile signal to a user in response to the detection of the blood vessel.

5. The system of claim 1, wherein the coupler comprises at least one of a first membrane configured to reflect the sound beam, a second membrane configured to pass the sound beam through a skin surface, and a window configured to pass the sound beam through a skin surface.

6. The system of claim 1, wherein the coupler includes a chamber that contains a coupling material.

7. The system of claim 1, wherein the coupler includes a reflective portion that reflects the sound beam from the transducer assembly to the blood vessel, and from the blood vessel to the transducer portion.

8. The system of claim 1, wherein the coupler is at least one of attachable and detachable from the transducer assembly.

9. The system of claim 1, wherein the coupler is capable of disassembly.

10. The system of claim 1, wherein the guideway is configured with a slot that enables separation of the coupler and the needle.

11. The coupler of claim 1, wherein the coupler is disposable.

12. A needle insertion method, comprising:
transmitting a sound beam along a first axis, the focal region of the sound beam being comparable in diameter to or smaller than a blood vessel;
reflecting the sound beam along a second axis to and from the blood vessel located beneath a skin surface;
receiving the reflected sound beam along the first axis;
processing the reflected sound beam to detect a Doppler shift induced by blood flow in the blood vessel to detect the location of the blood vessel; and
responsive to the detection, receiving a needle in a guideway that is oriented parallel to the second axis and offset a fixed distance from the second axis.

13. The method of claim 12, further comprising contacting the blood vessel with the needle proximally to where the sound beam was reflected from the blood vessel.

14. The method of claim 12, wherein transmitting includes transmitting a pulsed ultrasonic beam.

15. The method of claim 12, further including providing feedback to a user in response to the detection.

16. The method of claim 15, wherein providing feedback includes providing the feedback at least until the needle contacts the blood vessel.

17. The method of claim 16, further including providing at least one of an audible sound, a visual display signal, and a tactile signal to a user in response to the detection.

18. A needle insertion method, comprising:
- means for transmitting a sound beam along a first axis, the focal region of the sound beam being comparable in diameter to or smaller than a blood vessel;
- means for reflecting the sound beam along a second axis to and from the blood vessel located beneath a skin surface;
- means for receiving the reflected sound beam along the first axis;
- means for processing the reflected sound beam to detect a Doppler shift induced by blood flow in the blood vessel to detect the location of the blood vessel; and
- means for receiving a needle along a third axis that is parallel to the second axis and offset a fixed distance from the second axis.

19. The coupler of claim 18, wherein the means for receiving a needle is a guideway.

20. The coupler of claim 19, wherein the guideway is slotted.

21. The coupler of claim 18, wherein the means for reflecting the sound beam further comprise a chamber configured to contain a coupling material, a reflective portion, a window, and a transducer assembly attachment means.

22. The coupler of claim 18, wherein the means for reflecting the sound beam further comprise a reflective membrane, a skin surface interface membrane, a chamber configured to contain a coupling material, and a transducer assembly attachment means.

* * * * *